United States Patent [19]
Deasley et al.

[11] 3,951,601
[45] Apr. 20, 1976

[54] DETERMINATION OF SOFTENING TEMPERATURES FOR THIN FILMS

[75] Inventors: Peter John Deasley, Newmarket; Howard Donald Curtis, Swavesey; Paul Castle, Willingham, all of England

[73] Assignee: Decca Limited, London, England

[22] Filed: May 1, 1975

[21] Appl. No.: 573,765

[52] U.S. Cl. .............................................. 73/17 R
[51] Int. Cl.² ........................................ G01N 25/04
[58] Field of Search .......................... 73/17 R, 81

[56] References Cited
UNITED STATES PATENTS
3,187,556  6/1965  Ehlers .................................. 73/17
3,742,755  7/1973  Smith .................................. 73/17

FOREIGN PATENTS OR APPLICATIONS
738,606  10/1955  United Kingdom .................. 73/81

Primary Examiner—Herbert Goldstein
Attorney, Agent, or Firm—Edward F. Connors

[57] ABSTRACT

A technique is provided for the determination of the temperature at which thin films of, for instance plastics materials, soften. The thin film under test is disposed upon a conductive substrate and forms the dielectric of a capacitor, one electrode of which is provided by the conductive substrate, and the other electrode of which is provided by an electrically conductive indentor which rests on the surface with a preset loading. The thin film is heated, and its temperature is monitored, the capacitance between the substrate and the indentor is also monitored. When the material of the film softens, the indentor penetrates the film and this produces a sharp increase in the capacitance. By noting the temperature at which this sharp rise in capacitance occurs, an accurate value for the softening temperature of the thin film is obtained.

19 Claims, 3 Drawing Figures

DETERMINATION OF SOFTENING TEMPERATURES FOR THIN FILMS

This invention relates to a technique, incorporating a method and apparatus, for the determination of the softening temperature of thin films.

The technique is particularly applicable to thin films of plastics materials. In the plastics surface coatings industry there is often the need to measure the softening temperature of thin films. The softening temperature of bulk samples of the test materials may be determined by any of a number of well established experimental techniques. However, the results so obtained cannot usually be applied to the same material in a thin film form, and these known methods are not suitable for testing the same materials in that form.

The proposed method of the invention consists in monitoring the capacitance between a suitably loaded indentor and an electrically conductive substrate which has been coated with a thin film of the material under test. This material then forms the dielectric of the capacitor, the indentor resting on the surface of the film. If the film is heated it will eventually soften, allowing the indentor to penetrate the film. The capacitance between the indentor and the substrate will at this point increase rapidly and indicate that the softening temperature has been reached.

According to the invention, therefore, there is provided a method for determining the softening temperature of a thin film of material deposited upon a conductive substrate, comprising heating said thin film, measuring the temperature therefor and monitoring the capacitance between said substrate and an electrically conductive indentor resting on the surface of the thin film, and ascertaining the temperature at which the capacitance substantially increases, said temperature being the softening temperature of the thin film.

The film and substrate may be disposed in a container, the container being heated, and the temperature of the space within the container being measured. Alternatively, the film may be heated by passing an electric current through the substrate, the temperature of the film being measured in the vicinity of the indentor by means, for example, of a point thermocouple.

According to the invention there is also provided apparatus for the determination of the softening temperature of a thin film of material comprising a conductive substrate on which said film is deposited, means for heating said film, means for measuring the temperature thereof, an electrically conductive indentor which is adapted to rest on the thin film, and means for monitoring the capacitance between said indentor and said substrate.

Means may be provided for adjusting the force with which the indentor rests on the thin film.

The film and substrate may be disposed within a container, the means for heating the film comprising means for heating the container, and the means for measuring the temperature comprising means for measuring the temperature of the space within the container. Alternatively, the means for heating may comprise means for passing an electric current through the substrate, the means for measuring the temperature comprising a temperature sensing device, for instance a point thermocouple, for sensing the temperature of the film at a point in the vicinity of the indentor. The indentor may comprise a stylus mounted on an arm which is pivotable with respect to the film. The film may be flat and means may be provided for supporting the film and substrate in a horizontal orientation, the arm being pivotable in a vertical plane. Means may be provided for adjusting the force with which the said stylus bears on the film surface. The substrate and film may be disposed on a rigid circular disc, a rotatable support member for the disc being provided in the container, and the arm being also pivotable in a horizontal plane, whereby the stylus can be positioned at any desired point on the film surface.

The means for passing current through the conductive substrate may comprise two radially spaced annular bands of another conductive material disposed on and electrically connected with the substrate, which is itself disposed on the rigid disc, and means for making electrical contact with and passing current between said annular bands.

A preferred embodiment of the invention will now be described by way of example, with reference to the accompanying drawings, in which.

Figure 1:
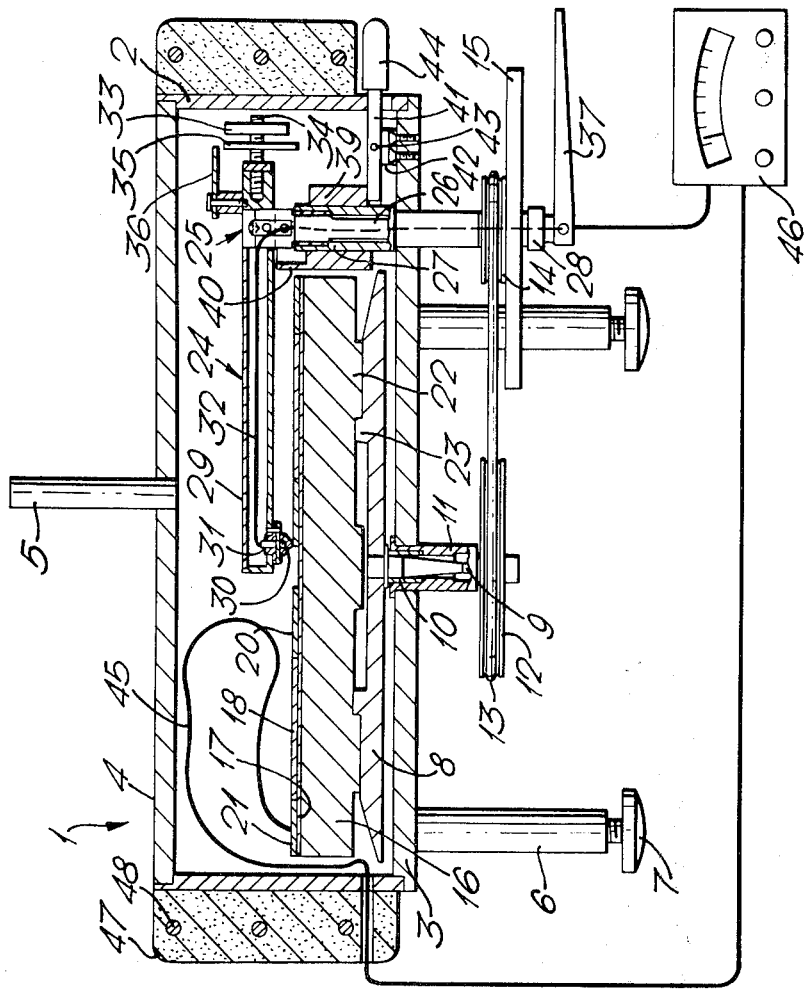
FIG. 1 is a part sectional and part elevational view of an apparatus for determining the softening temperature of thin films.

The apparatus comprises a container 1 having a cylindrical sidewall 2, a circular base 3, and a transparent removable lid 4. The lid may be of glass and is provided with an upwardly projecting handle 5 to facilitate removal for access to the interior of the container. The container stands on three legs 6 provided with adjustable feet 7 for levelling purposes. Within the container 1 is a circular disc plate 8 rotatably mounted on the base 3 by means of a central spindle 9 fixed at its upper end to the disc plate, and rotatably arranged in a bushing 10 which is itself located in a spindle housing 11 fixed in relation to the container base and projecting downwardly therefrom. A pulley 12 attached to the lower end of the spindle is rotatably coupled, by means of a belt 13 to a drive pulley 14 which is rotatably by hand by means of an annular flange 15.

Figure 2:
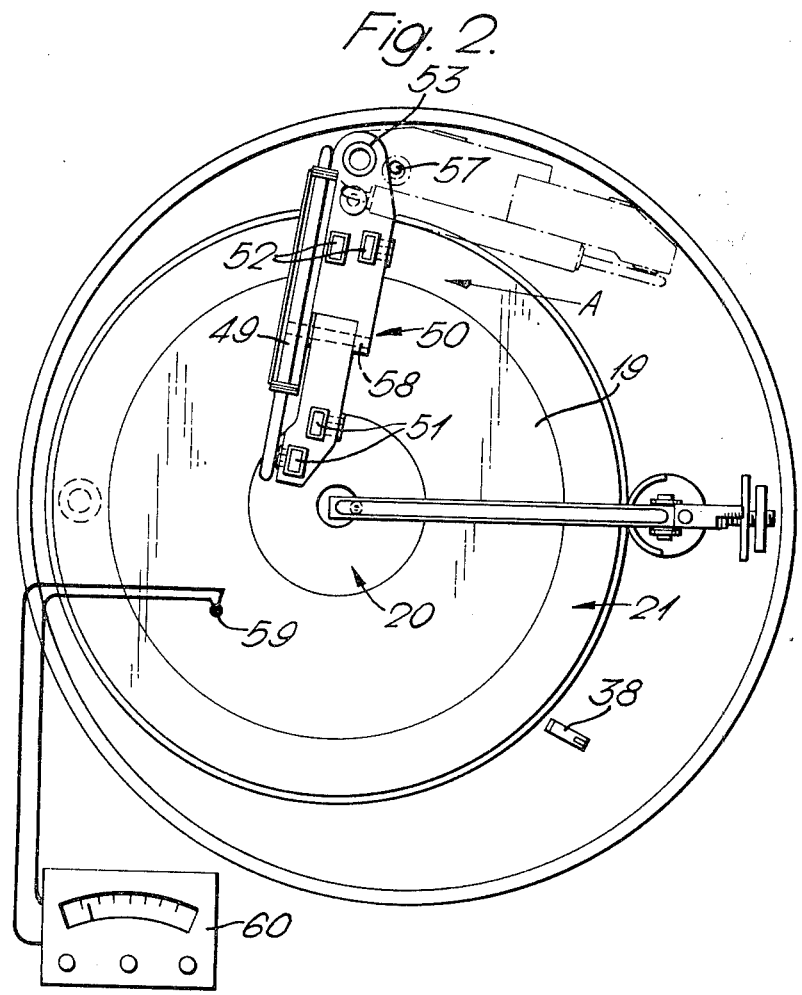
FIG. 2 is a plan view of the apparatus shown in FIG. 1, with a cover removed therefrom.
Figure 3:
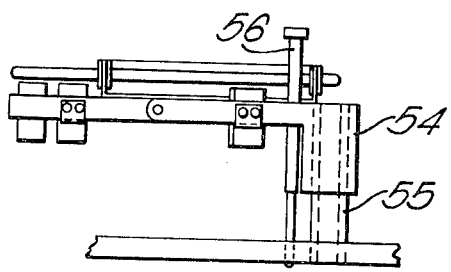
FIG. 3 is a side elevational view of a part of the apparatus as shown in FIG. 2, as seen in the direction of arrow A.

A sample disc carrying the film to be tested comprises a glass disc 16 having on its upper surface a substrate 17, in the form of a thin film of conductive material. The thin film 18 of test material is deposited on top of the conductive substrate 17. In this embodiment an inner and an outer annular thin film band, 20 and 21, respectively, of another conductive material are arranged on top of the film 17 in electrical contact therewith, for a purpose to be explained hereinafter, and the thin film of test material comprises a wide annular ring 19 (see FIG. 2) between the two bands 20 and 21. In this embodiment the substrate 17 is of chromium and the two bands 20 and 21 are of gold.

The sample disc has on its lower surface an annular step 22 whose inner diameter corresponds substantially with the outer diameter of a corresponding step 23 on the disc plate 8, whereby the sample disc may be accurately centred.

An arm 24 is pivotally mounted by means of a knife-edge support 25 on an arm support shaft 26 which is rotatably mounted in a shaft housing 27 passing through the container base at a point close to the edge of the disc plate 8. The drive pulley 14 is rotatably mounted at the lower end of the shaft housing, and is retained by an end collar 28.

The arm 24 comprises an elongate hollow metal member having a removable cover strip 29. At its inner end, the arm carries a metal stylus 30, constituting an indentor, removably attached to a stylus stud 31 which projects into and is insulated from the metal arm, and which has electrically connected thereto, one end of a first test lead 32. This lead passes along the inside of the arm, down the inside of the arm support shaft, and projects from the lower end thereof.

The arm is counterbalanced by a counterbalance weight 33 which is mounted on a threaded stud 34 projecting outwardly from the outer end of the arm 24 on the side of the knife-edge support remote from the stylus. The stylus loading can be adjusted by moving an adjustment weight 35 along the threaded stud, the loading being read from a scale 36 mounted on the arm.

An arm lever 37 is attached to the lower end of the arm support shaft 26, for manual rotation of the arm about the axis of that shaft, whereby the stylus may be appropriately positioned with respect to the surface of the sample disc. An arm rest 38 is mounted on the container base for retaining the arm in an inoperative position when appropriate.

Means are provided for raising the arm, thereby to lift the stylus from the thin film when necessary. This means comprises a cylindrical collar 39 arranged to slide up and down the outside of the shaft housing 27, and having an upstanding semi-cylindrical flange 40 whose upper edge will engage the under side of the arm in the lifted position, causing the latter to pivot about the knife edge whereby the stylus will be raised. For raising the collar an arm lever 41 is pivotally mounted on a pivot block 42 attached to the container base, and is pivotable in a vertical plane about a horizontal pivot pin 43. The arm lever engages at its inner end in a notch in the lower edge of the collar 39 (thereby preventing rotation of the latter about the axis of the shaft housing) and projects through an aperture in the container sidewall at its outer end, a handle 44 of heat resistant material being connected thereto. Depression of the handle 44 causes lifting of the arm.

Electrical connection to the chromium film or substrate, is made by way of an attachment of one end of a second test lead 45 to one or other of the gold rings. This second test lead passes through the container wall 2 and the two test leads 32 and 45 are connected to an A.C. bridge 46 which measures the capacitance between the stylus and the substrate. Such bridges are readily obtainable, and no further description thereof is considered necessary here.

Means for heating the container and for measuring the temperature inside it are provided. The means for heating may comprise a flexible elongate wrap-around blanket 47 arranged on the outer surface of the container wall, and having heating elements 48 therein. The corresponding temperature measuring means comprises a simple mercury-in-glass thermometer 49 appropriately mounted inside the container.

The film may alternatively be heated by passing current through the chromium substrate and it is particularly, for this purpose that the gold bands 20 and 21 are provided. Further, a heating arm 50 is provided (omitted from FIG. 1 for clarity), this arm having two pairs of carbon contact brushes, an inner pair 51 for contacting the inner gold ring 20, and an outer pair 52 for contacting the outer gold band 21. The heating arm may be swung about an end pivot 53 between an operative position, as shown in full lines in FIG. 2 and a non-operative position as shown in broken lines in FIG. 2. The end pivot 53 comprises a downwardly extending collar 54 rigidly connected with the arm, and fitting over and sliding on a hollow pivot stem 55, whereby the heating arm may be raised before being pivoted. A locating pin 56 retains the heating arm in its operative or non-operative position by engaging in one of the two recesses 57 in the container base. The inner part of the arm carrying the inner pair of carbon brushes 51 is hinged at 58 to the outer part carrying the outer pair of carbon brushes 52 and the collar 54, to ensure good contact between the carbon brushes and the two gold bands in the event that these two bands are not exactly coplanar. Contact pressure of the brushes on the gold bands due to the weight of the arm 50 is sufficient to ensure good electrical contact.

The thermometer 49 is mounted by a bracket attached to the outer part of the heating arm, and power leads, (not shown) attached to the brushes pass along the heating arm and down through the pivot stem 55, and thence to a suitable power source.

The method of operating the apparatus is as follows. With the lid 4 removed and the arms 23 and 50 swung to their inoperative positions a sample disc is correctly located on the disc plate by means of the annular steps 22 and 23 and the test lead 45 is attached to the outer gold band. The disc plate is positioned as described by rotating the drive pulley 14 by means of the flange 15. The arm 23 is disengaged from the arm rest 38, and, with the arm lever handle depressed, the arm is appropriately positioned by means of the arm lever 37. The stylus is then lowered onto the thin film surface, assuming that the counterbalance and adjustment weights 33 and 35 have previously been set for the desired stylus loading.

If the heating blanket is to be used the lid 4 is then replaced and heating power supplied to the elements 48. The temperature as shown by the thermometer 49 and the capacitance as registered on the read-out scale of the AC bridge 46 are continuously monitored. When the softening temperature of the thin film is reached, the stylus penetrates the film and the AC b7idge registers a sudden increase in capacitance. The temperature given by the thermometer 47 is then the required softening temperature.

If, however, the film is to be heated by passing current through the substrate, the heating arm 50 is lifted and pivoted to its operative position, the locating pin 56 is then being engaged in the appropriate recess 57.

A thermocouple shown schematically at 59 is then placed on the surface of the thin film close to the stylus, so that the temperature at the stylus itself is monitored. The leads from the thermocouple pass out of the container and are connected to a suitable measuring circuit 60 calibrated in degrees (temp).

The lid 4 is replaced and the film is heated by supplying power to the carbon brushes. Again the temperature and capacitance are monitored, and when the capacitance suddenly increases thy temperature is noted.

The loading on the stylus is of importance as it allows film softening to be distinguished from a creep phenomenon. Thus, when softening occurs, the rate of increase of capacitance is considerably greater than that encountered during a creep process.

Having performed one determination as described, the arm 23 may be raised, and the sample disc repositioned by rotating the drive pulley 14, so that another point on the thin film may be tested.

The above described technique is of wide application and, with care can be used on films as thin as 1–2 microns.

We claim:

1. A method for determining the softening temperature of a thin film of material deposited on a conductive substrate, comprising heating said thin film, measuring the temperature thereof and monitoring the capacitance between said substrate and an electrically conductive indentor resting on the surface of the thin film, and ascertaining the temperature at which that capacitance substantially increases, said temperature being the softening temperature of the thin film.

2. A method according to claim 1 wherein said film and substrate are placed in a container said film is heated by heating the container, and the temperature of the film is measured by measuring the temperature within the container.

3. A method according to claim 1 wherein said thin film is heated by passing an electrical current through said substrate, and the temperature of the film is measured by measuring directly the temperature at various points on the thin film surface.

4. A method according to claim 3, wherein current is passed through said substrate by means of a pair of spaced conductive electrodes electrically connected to a surface of the substrate, the point at which said indentor rests on the thin film lying between said electrodes.

5. A method according to claim 1, wherein said substrate is disposed on a surface of a rigid non-conductive support element.

6. A method according to claim 5, wherein said support element comprises a flat disc mounted horizontally which is rotated around a central vertical axis for selecting the particular point on the thin film surface at which the indentor rests.

7. A method according to claim 1 wherein the indentor is carried by an arm mounted for pivotal movement in a vertical plane on a low friction support.

8. A method according to claim 7, wherein the force with which the indentor rests on the thin film surface is adjustable.

9. Apparatus for the determination of the softening temperature of a thin film of material comprising a conductive substrate on which said film will be deposited, means for heating the film, means for measuring the temperature thereof, an electrically conductive indentor which is adapted to rest on the thin film, and means for monitoring the capacitance between said indentor and said substrate.

10. Apparatus according to claim 9 including means for adjusting the force with which the indentor rests on the thin film.

11. Apparatus according to claim 9, wherein said means for heating the thin film comprises means for heating the container, and wherein the means for measuring the temperature of the thin film comprises means for measuring the temperature of the space within the container.

12. Apparatus according to claim 9, wherein the means for heating the thin film comprises means for passing an electrical current through the substrate, and wherein the means for measuring the temperature of the thin film includes temperature sensing means adapted to be positioned in the vicinity of the indentor, thereby to sense the temperature of that part of the film in that vicinity.

13. Apparatus according to claim 12, wherein mounted on, and in electrical contact with a surface of said substrate, is a pair of spaced conductive electrodes, between which at least part of the thin film to be tested will be deposited.

14. Apparatus according to claim 9 including a rigid non-conductive support element having a support surface on which said conductive substrate is disposed.

15. Apparatus according to claim 14, wherein support element comprises a disc, said support surface is flat, and wherein there are provided means for rotatably mounting said disc with said support surface in a horizontal plane.

16. Apparatus according to claim 13, including a rigid non-conductive support element having a support surface on which said conductive substrate is disposed, wherein said support element comprises a disc, said support surface is flat, and wherein there are provided means for rotatably mounting said disc with said support surface in a horizontal plane.

17. Apparatus according to claim 16 wherein said conductive electrodes comprise a pair of radially spaced annular bands disposed on said surface of the substrate, and wherein there are provided means for electrically contacting and for passing current between said bands and through the substrate therebetween.

18. Apparatus according to claim 9 including an arm which is mounted on a low friction support for pivotal movement in a vertical plane and which carries the indentor at a point remote from said support.

19. Apparatus according to claim 18 wherein said arm is also mounted for pivoting in a horizontal plane, whereby the position of the indentor on the thin film will be selectable.

* * * * *